United States Patent
Cohen et al.

(10) Patent No.: US 10,849,851 B2
(45) Date of Patent: *Dec. 1, 2020

(54) STABLE ORAL SOLUTIONS FOR COMBINED API

(71) Applicant: Pharnext, Issy les Moulineaux (FR)

(72) Inventors: Daniel Cohen, Le Vésinet (FR); Ilya Chumakov, Vaux le Penil (FR); Serguei Nabirochkin, Chatenay Malabry (FR); Viviane Bertrand, Paris (FR)

(73) Assignee: Pharnext, Issy-les-Moulineaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/374,375

(22) Filed: Apr. 3, 2019

(65) Prior Publication Data

US 2019/0290578 A1    Sep. 26, 2019

Related U.S. Application Data

(63) Continuation of application No. 14/896,214, filed as application No. PCT/EP2014/061664 on Jun. 5, 2014, now Pat. No. 10,300,015.

(30) Foreign Application Priority Data

Jun. 5, 2013 (EP) .................... 13170583

(51) Int. Cl.
| | | |
|---|---|---|
| A61K 9/00 | (2006.01) | |
| A61K 47/12 | (2006.01) | |
| A61K 47/14 | (2017.01) | |
| A61K 47/26 | (2006.01) | |
| A61K 9/08 | (2006.01) | |
| A61K 31/485 | (2006.01) | |
| A61K 31/047 | (2006.01) | |
| A61K 31/195 | (2006.01) | |
| A61K 31/197 | (2006.01) | |

(52) U.S. Cl.
CPC .......... *A61K 9/0053* (2013.01); *A61K 9/0095* (2013.01); *A61K 9/08* (2013.01); *A61K 31/047* (2013.01); *A61K 31/195* (2013.01); *A61K 31/197* (2013.01); *A61K 31/485* (2013.01); *A61K 47/12* (2013.01); *A61K 47/14* (2013.01); *A61K 47/26* (2013.01)

(58) Field of Classification Search
CPC .. A61K 31/047; A61K 31/195; A61K 31/197; A61K 31/485; A61K 47/12; A61K 47/14
See application file for complete search history.

(56) References Cited

U.S. PATENT DOCUMENTS

| | | |
|---|---|---|
| 7,592,372 B2 | 9/2009 | Osugi |
| 8,716,269 B2 | 5/2014 | Cohen et al. |
| 8,992,891 B2 | 3/2015 | Cohen et al. |
| 9,393,241 B2 | 7/2016 | Cohen et al. |
| 9,427,436 B1 | 8/2016 | Cohen et al. |
| 9,566,275 B2 | 2/2017 | Cohen et al. |
| 10,300,015 B2* | 5/2019 | Cohen ............... A61K 31/485 |
| 2003/0069213 A1 | 4/2003 | Ii et al. |
| 2005/0038062 A1 | 2/2005 | Burns et al. |
| 2005/0187290 A1 | 8/2005 | Fontes et al. |
| 2005/0220863 A1 | 10/2005 | Han et al. |
| 2007/0099947 A1 | 5/2007 | Dean et al. |
| 2007/0110801 A1 | 5/2007 | Perovitch et al. |
| 2007/0299098 A1 | 12/2007 | Tanabe |
| 2008/0206332 A1 | 8/2008 | Kidney et al. |
| 2008/0255062 A1 | 10/2008 | Fernyhough |
| 2012/0040940 A1 | 2/2012 | Cohen et al. |
| 2012/0088744 A1 | 4/2012 | Cohen et al. |
| 2012/0270836 A1 | 10/2012 | Cohen et al. |
| 2013/0059876 A1 | 3/2013 | Angeli et al. |
| 2013/0085122 A1 | 4/2013 | Cohen et al. |
| 2013/0090307 A1 | 4/2013 | Cohen et al. |
| 2014/0178463 A1 | 6/2014 | Cohen et al. |
| 2015/0157626 A1 | 6/2015 | Cohen et al. |
| 2017/0165256 A1 | 6/2017 | Cohen et al. |
| 2018/0000813 A1 | 1/2018 | Cohen et al. |

FOREIGN PATENT DOCUMENTS

| | | |
|---|---|---|
| CA | 2727064 A1 | 12/2009 |
| DE | 102006016990 A1 | 10/2007 |
| EP | 0778023 A1 | 6/1997 |
| EP | 2065038 A1 | 6/2009 |
| EP | 2263665 A1 | 12/2010 |
| WO | WO 200020024 A2 | 4/2000 |
| WO | WO 2002049607 A2 | 3/2003 |
| WO | WO 2003077867 A2 | 9/2003 |
| WO | WO 2004006911 A2 | 1/2004 |
| WO | WO 2004019938 A1 | 3/2004 |
| WO | WO 2004103263 A2 | 12/2004 |
| WO | WO 2005032555 A2 | 4/2005 |

(Continued)

OTHER PUBLICATIONS

Bassi et al., "Encephalomyelitis with Thyrotoxicosis," Journal of Neurology, vol. 218, No Month Listed 1978 (pp. 293-295).
Berenbaum et al., "Synergy, Additivism and Antagonism in Immunosuppression: A Critical Review," Clinical & Experimental Immunology, vol. 28, No Month Listed 1977 (pp. 1-18).
Chambliss, W.G., Acetic Acid monograph and Sodium Acetate monograph, in Handbook of Pharmaceutical Excipients 5th ed., 2006, pp. 6-7, 654-655.
Chemidex Pharma Ltd., "Lyflex 5mg/5ml Oral Solution," retrieved from the internet: <http://emc.medicines.org.uk/emc/assets/c/html/DisplayDoc.asp?document_ID=14939>, Apr. 14, 2008 (10 pages).
Cintas et al., "Drug Therapy for symptomatic Relief in ALS—Quels Sont Les traitements Medicamenteux Syptomatiques?" Revue Neurologique, vol. 162, Jun. 1, 2006 (pp. 4S235-4S243).

(Continued)

*Primary Examiner* — James D. Anderson
(74) *Attorney, Agent, or Firm* — Andrea L.C. Reid; Joseph W. Arico; Dechert LLP (57) ABSTRACT

The present invention relates to a homogeneous, stable, and palatable pharmaceutical solution comprising baclofen, sorbitol and naltrexone.

35 Claims, 2 Drawing Sheets

(56) References Cited

FOREIGN PATENT DOCUMENTS

| WO | WO 2005053612 A2 | 6/2005 |
|---|---|---|
| WO | WO 2006117573 A1 | 11/2006 |
| WO | WO 2007134077 A2 | 11/2007 |
| WO | WO 2007134136 A2 | 11/2007 |
| WO | WO 2009068668 A1 | 6/2009 |
| WO | WO 2009153291 A1 | 12/2009 |
| WO | WO 2010139627 A1 | 12/2010 |
| WO | WO 2011054759 A1 | 5/2011 |
| WO | WO 2012117076 A2 | 9/2012 |
| WO | WO 2014195394 A1 | 12/2014 |

OTHER PUBLICATIONS

Coffey et al., "Familial Trigeminal Neuralgia and Charcot-Marie-Tooth Neuropathy—Report of Two Families and Review," Surgical Neurology, vol. 35, Jan. 1, 1991 (pp. 49-53).

Colombo et al., "Effects of the Combination of Naltrexone and Baclofen on Acquisition of Alcohol Drinking Behavior in Alcohol-Preferring Rats," Drug and Alcohol Dependence, vol. 77, No. 1, No Month Listed 2005 (pp. 87-91).

Gabreëls-Festen et al., "Charcot-Marie-Tooth disease type 1A: morphological phenotype of the 17p duplication versus PMP22 point mutations," Acta Neuropathologica, vol. 90, 1995, pp. 645-649.

Gallagher et al., "Persistent Effects of Mifepristone (RU-486) on Cortisol Levels in Bipolar Disorder and Schizophrenia," Journal of Psychiatric Research, vol. 42, No. 12, Oct. 1, 2008 (pp. 1037-1041).

Genetics Home Reference: Your Guide to Understanding Genetics Conditions "Charcot-Marie-Tooth Disease," Dec. 11, 2012 <http://ghr.nlm.nih.gov/condition/charcot-marie-tooth-desease/show/print> (15 pages).

Gironi et al., "A Pilot Trial of Low-Dose Naltrexone in Primary Progressive Multiple Sclerosis," Multiple Sclerosis, vol. 14, No. 8, Sep. 1, 2008 (pp. 1076-1083).

Graham et al., "A modified peripheral neuropathy scale: the Overall Neuropathy Limitations Scale," Journal of Neurology, Neurosurgery and Psychiatry, vol. 77, 2006, pp. 973-976.

Grandis et al., "Current Therapy for Charcot-Marie-Tooth Disease," Current Treatment Options in Neurology, vol. 7, No. 1, No Month Listed 2005 (pp. 23-31).

Herrmann et al., "Experimental Therapeutics in Hereditary Neuropathies: The Past, the Present and the Future," Neurotherapeutics, vol. 5, No. 4, Jan. 1, 2008 (pp. 507-515).

International Search Report and Written Opinion issued by the European Patent Office as International Searching Authority for International Application No. PCT/EP2008/066468 dated Mar. 3, 2009 (14 pages).

International Search Report and Written Opinion issued by the European Patent Office as International Searching Authority for International Application No. PCT/EP2010/057438 dated Nov. 4, 2010 (19 pages).

International Search Report and Written Opinion issued by the European Patent Office as International Searching Authority for International Application No. PCT/EP2014/061664 dated Jun. 30, 2014 (10 pages).

Jones, D., "Chapter 1: Pharmaceutical solutions for oral administration. In Pharmaceutics—Dosage Form and Design," 1E, 2008.

Kellner et al., "Myotonic Pupils in Charcot-Marie-Tooth Disease. Successful Relief Symptoms with 0.025% Pilocarpine," Archives of Ophthalmology, vol. 93, No. 11, No Month Listed 1975 (pp. 1141-1148).

Lees et al., "Baclofen in Parkinson's Disease," Journal of Neurology, Neurosurgery & Psychiatry, vol. 41, Jan. 1, 1978 (pp. 707-708).

Li et al., "Effect of Baclofen Combined with Neural Facilitation Technique on the Reduction of Muscular Spasm in Patients with Spinal Cord Injury," Neural Regeneration Research, vol. 2, No. 8, Aug. 2007 (pp. 510-512).

Magnaghi et al., "GABA Receptor-Mediated Effects in the Peripheral Nervous System—A Cross-Interaction with Neuroactive Steroids," Journal of Molecular Neuroscience, vol. 28, No. 1, No Month Listed 2006 (pp. 89-102).

Maxwell et al., "Two rapid and simple methods used for the removal of resins from 1.0 micron thick epoxy sections," Journal of Microscopy, vol. 112, 1978, pp. 253-255.

Meyer Zu Horste et al., "Antiprogesterone Therapy Uncouples Axonal Loss from Demyelination in a Transgenic Rat Model of CMT1A Neuropathy," Annals of Neurology, vol. 61, 2007, pp. 61-72.

Mhra, "Baclofen 5MG/5ML Oral Solution," Retrieved from the Internet <http://www.mhra.gov.nk/home/groups/par/documents/websiteresources/con094157.pdf> Aug. 2, 2010 (22 pages).

National Institute of Neurological Disorders and Stroke, "Charcot-Marie-Tooth Disease Fact Sheet," retrieved from the Internet: https://www.ninds.nih.gov/Disorders/Patient-caregiver-education/Fact-sheets/Charcot-Marie-Tooth-Disease-Fact-Sheet, Jan. 8, 2018.

Norris et al., "Trial of Baclofen in Amyotrophic Lateral Sclerosis," Archives of Neurology, vol. 36, Nov. 1, 1979 (pp. 715-716).

Pharminfotech, "Baclofen," Formulation in Pharmacy Practice—eMixt, Retrieved from the Internet <http://www.pharminfotech.co.nz/manual/Formulation/mixtures/baclofen.html> Aug. 31, 2011 (2 pages).

Pomara et al., "Mifepristone (RU 486) for Alzheimer's Disease," Neurology, vol. 58, No. 9, May 1, 2002 (p. 1436).

RightDiagnosis.com http://www.rightdiagnosis.com/n/neuropathy/subtypes.htm. Accessed Feb. 28, 2014 (pp. 1-9).

Rivlin et al., "Objective clinical assessment of motor function after experimental spinal cord injury in the rat," Journal of Neurosurgery, vol. 47, 1977, pp. 577-581.

SciFinder® Sorbitol Search Results (2018). Copyright © 2018 American Chemical Society (ACS).

Sereda et al., "A transgenic rat model of Charcot-Marie-Tooth disease," Neuron, vol. 16, 1996, pp. 1049-1060.

Shy et al., "Reliability and validity of the CMT neuropathy score as a measure of disability," Neurology, vol. 64, 2005, pp. 1209-1214.

Slavick et al., "In Vitro Correlates of in Vivo Rapamycin Therapy in Patients with Multiple Sclerosis," Clinical Immunology, vol. 119, Jan. 1, 2006 (p. S113).

Stella et al., "Prodrug Strategies to Overcome Poor Water Solubility," Advanced Drug Delivery Reviews 59, No Month Listed 2007 (pp. 677-694).

Weimer et al., "Medication-Induced Exacerbation of Neuropathy in Charcot-Marie-Tooth Disease," Journal of Neurological Science, vol. 242, No. 1-2, No Month Listed 2006 (pp. 47-54).

Wilcock et al., "A Placebo-Controlled, Double-Blind Trial of the Selective AB-42 Lowering Agent, Flurizan (MPC-7869, (R)-flurbiprofen) in Patients with Mild to Moderate Alzheimer's Disease," Alzheimer's & Dementia: The Journal of the Alzheimer's Association, vol. 1, No. 1, Jul. 1, 2005 (p. S95) abstract.

Zu Horste et al., "Myelin Disorders: Causes and Perspectives of Charcot-Marie-Tooth Neuropathy," Journal of Molecular Neuroscience, vol. 28, No. 1, No Month Listed 2005 (pp. 77-88).

* cited by examiner

STABLE ORAL SOLUTIONS FOR COMBINED API

The present invention relates to novel pharmaceutical compositions comprising baclofen, sorbitol and naltrexone and the uses thereof.

The novel pharmaceutical compositions of the invention are useful in the treatment of nervous system diseases such as e.g. Charcot-Marie-Tooth disease, neuropathic pain, drug or alcohol withdrawal, or Parkinson's disease.

It has been recently shown (WO2010/139627) that an oral combinatorial treatment based on the oral administration, as active ingredients, of baclofen, sorbitol and naltrexone is efficient in treating Charcot-Marie-Tooth disease (CMT). As these active pharmaceutical ingredients (APIs) may be used in highly heterogeneous amounts, there is a need for a galenic form that offers a homogeneous distribution of APIs in the medicament while respecting physico-chemical requirements of each drug to ensure their stability and, being easily swallowed, encouraging good compliance.

Baclofen is a muscle relaxant which has been approved for treating transient spasticity and which is currently under development for the treatment of alcohol dependence and alcohol withdrawal. It is a derivative of gamma-aminobutyric acid (GABA) and acts as an agonist for the GABAB receptors [1]. It has been commercialized under various pharmaceutical forms as muscle relaxant. It is currently marketed under tablet form and solution (by instance, Lioresal, 5 mg/5 mL) for oral administration. Liquid formulations for infusion have also been developed, as well as creams for topical application in conjunction with other muscle relaxant, anti-inflammatory and/or analgesic drugs. Baclofen is known as poorly soluble in aqueous solutions and strong acids or bases required for increasing baclofen solubility are often harmful and incompatible with drug safety requirements [2]. Intrathecal treatment (such as Lioresal intrathecal, developed by Novartis) is a treatment of choice in patients who are unresponsive to or cannot tolerate oral therapy [3]. Moreover this route is believed to be more efficient than oral route in treating severe spastic events. In this regard, several artificial cerebrospinal fluids have been also developed for intrathecal administration of baclofen. WO2008/157288 discloses liquid formulations for baclofen concentration ranking from 2 mg/mL to 10 mg/mL, consisting in a complex multivalent physiological ion solution.

Sorbitol, or glucitol, is a natural sugar-alcohol naturally found in some fruits and berries. It is mainly used as a food additive (E420), highly soluble in water whereas poorly soluble in ethanol, commonly used as sweetener, notably as sugar-substitute in diet foods, although the sweetness of sorbitol is poor (about half that of sucrose) compared to other sugar-substitute such as stevioside (about 200 times higher than sucrose) [4]. Sorbitol may also serve as humectant, viscosity controlling, bulking and preservative agent. In this context it can be provided in its crystalline form, powder or in solution, as a 70% weight solution. Because of these features and of its high stability, it is broadly used in processed foods, cosmetics and pharmaceuticals. In Europe, sorbitol is also commercialized as an osmotic laxative medicine. Liquid rectal formulation is marketed at a concentration of 4.465 g/5 mL. Sorbitol is also used in irrigation solution (for example, Sorbitol Irrigant, 3.3 g/100 mL).

Naltrexone is a broad-spectrum opioid antagonist that is mainly used in the treatment of alcohol and opiate dependences. It is a small molecule able to cross the blood brain barrier. Its hydrochloride salt is the preferred form and pharmaceutical forms encompass oral forms (e.g. capsules, solution, and polymeric microspheres), injectable formulation as well as implants. Naltrexone mainly reduces heavy drinking and craving behaviors [5] and acts by blocking the effects of heroin. Studies have shown that the compliance is more related to the patient population than the administration route (implanted sustained release devices versus oral tablets) [6-8]. Oral solutions for naltrexone are provided at concentrations ranking from 1 to 5 mg per mL.

There is a wide variety of dosage forms for administering drugs or combinations of drugs. The choice of the galenic form for a medicine is governed by several criteria which are for example: the inherent physico-chemical properties of the API and the potential compatibility issues between mixed APIs and/or the excipients, metabolism of the API, compatibility between patient's condition and the route of administration (for instance the patient's capacity to swallow), potential impact of the dosage form on the compliance of patients (palatability, convenience of use), development and production costs (the medicine should be as affordable as possible for patient) and storage requirements.

Most common oral dosage forms are tablets, capsules, and liquid formulations.

Because of the ease and convenience of their use, tablets account for most of the dosage form of the majority of medicines. They are solid dosage forms containing the API(s) and most often excipient(s) and/or carrier(s) which can be molded or compressed to obtain tablets of various sizes and shapes.

Capsules are another oral dosage form consisting in a shell within which API(s) are enclosed, in a powder or granular form. Nevertheless, the latter may have the inconvenient to be hard to swallow, especially for children, elderly persons or patients with a swallowing-affecting disease especially when API quantities necessitate large conditioning.

Suspensions are liquid formulations comprising not soluble solid particles dispersed in a solvent. Suspensions can be sold in liquid form which needs to be well shaken before use to avoid variability in dosage. Alternatively, they can be dispensed in a solid form (unit doses of powder) to be diluted upon use. Suspensions are also used in the preparation of tablets implying the use of a carrier excipient which is solid below a given temperature and liquid above another. This allows obtaining tablets within which active pharmaceutical ingredients are homogeneously dispersed.

Solutions are also liquid formulations within which molecules of APIs and other compounds such as excipients are typically homogeneously dispersed in a solvent. The difference with suspensions is the complete dissolution of API(s) in the vehicle. Pharmaceutical syrups are viscous liquids comprising a minimal dose of sucrose as defined in the pharmacopeia and at least one API. When medical concerns impede the use of sugar, sucrose is replaced by sugar substitutes or artificial sweetener admixed with a thickener. A concern with solutions is that APIs are more susceptible to chemical instability than in the other dosage forms. Moreover solutions need to be carefully handled to avoid potential microbial contaminations that may provoke degradation of APIs and/or cause patient intoxication.

To date, there is no formulation combining baclofen, sorbitol and naltrexone in a sole, stable and compliance-compatible pharmaceutical product. As stated above, baclofen and naltrexone are commercialized under liquid as well as solid formulations (e.g. Lioresal, Antaxone). Sorbitol is commercialized as a powder (Sorbitol Delalande, 5 g, Sanofi Aventis) to be used as an oral suspension or in a liquid form for rectal injection (Microlax).

Thus, there is an important need for a stable, homogeneous despite of great differences between the APIs concentrations, and compliance promoting formulation of such medicines suitable for the long term treatment of CMT, which is an orphan invalidating chronic disease.

SUMMARY OF THE INVENTION

The invention relates to novel oral compositions suitable for administration of combined APIs such as baclofen, sorbitol and naltrexone. The compositions are stable over time and particularly adapted for repeated intake in human subjects.

More particularly, an object of the invention resides in a pharmaceutical composition comprising, in the form of a solution:
baclofen, sorbitol, and naltrexone,
an acetate or citrate buffer having a pH comprised between 4 and 7, preferably between 4.5 and 5.5, and
optionally, at least one preservative and/or at least one flavoring agent.

A further object of the invention relates to a method for preparing a composition as defined above, comprising providing baclofen, sorbitol and naltrexone and admixing said active ingredients in solution in a citrate or acetate buffer having a pH comprised between 4 and 7.

The compositions of the invention may comprise further ingredients or excipients. They may be formulated in any suitable device such as a tube, flask, plastic or glass unit doses, stick packs, ampoule, pipette, etc.

Another object of the invention resides in a method for treating CMT in a human subject, comprising administering to the subject a composition of the invention.

DETAILED DESCRIPTION OF THE INVENTION

The present invention relates to novel pharmaceutical compositions in the form of liquid solutions comprising baclofen, sorbitol and naltrexone as active pharmaceutical ingredients ("APIs"). More specifically, the liquid solutions of the invention comprise the APIs, a buffer solution having a pH comprised between 4 and 7, preferably a citrate or acetate buffer solution, and, optionally, at least one preservative and/or at least one flavoring agent. As documented, such liquid formulations allow stable and homogeneous combination of said at least three drugs, even when used at very different relative concentrations, for instance of about 8.6/300/1 (weight ratio, respectively), and favors compliance.

Definitions

Within the context of this invention, the term "solution" refers to a mixture of one or more substances dispersed molecularly (i.e., dissolved) in a dissolving liquid medium or vehicle. The solution is preferably homogeneous, in the sense that each API is essentially uniformly distributed and concentrated in the solution. The liquid solution may be viscous (such as syrup) or not. As already mentioned, a liquid solution differs from a suspension which comprises solid particles dispersed throughout a liquid phase in which they are not soluble.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance, microbial growth, and/or color as exemplified in the experimental section. Typically, compositions according to the invention are considered as stable if at least 95% of the initial concentration of each of the APIs is found after 4 weeks at 25° C., and/or if no substantial change in the appearance of the solution is observed during such a period of time and under such temperature conditions. Stability is more preferably assessed under 60% relative humidity conditions.

Compositions

The invention relates to pharmaceutical compositions in the form of liquid solutions, suitable for oral intake, which comprise:
baclofen, sorbitol and naltrexone,
a buffer solution having a pH comprised between 4 and 7, preferably a citrate or acetate buffer solution, and
optionally, at least one preservative and/or at least one flavoring agent.

As exemplified in the experimental section, such liquid formulations favor the homogeneous dispersion of the APIs, are not prone to microbial contamination, and show a good stability for each of the APIs. Accordingly, the formulation of the three active ingredients in a unique dosage form is of great interest in the case of this medicine which may need to be taken all life long and for which a good compliance is therefore necessary. In a particular embodiment, the unit dosage form comprises 1, ½, ⅓ or ¼ of the daily therapeutic dose of the composition. In a preferred embodiment, the unit dosage form comprises half the daily therapeutic dose of the composition.

The Active Pharmaceutical Ingredients

The invention relates to novel compositions comprising, as APIs, a combination of at least baclofen, sorbitol, and naltrexone. Illustrative CAS number(s) are provided in table 1 below.

TABLE 1

| Active pharmaceutical ingredients | CAS number |
|---|---|
| Baclofen | 63701-56-4, 1134-47-0 |
| Sorbitol | 50-70-4 |
| Naltrexone | 16676-29-2, 16590-41-3 |

In the compositions of the invention, the APIs may be either in form of the chemical compounds as specifically named or in the form of any acceptable salts, hydrates, derivatives, isomers, racemates, conjugates and/or pro-drugs thereof.

The term "salt" refers to a pharmaceutically acceptable and relatively non-toxic, inorganic or organic acid or base addition salt of the APIs of the composition of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts include those in which the compound functions as an acid and is reacted with an appropriate base to form, e.g., sodium, potassium, calcium, magnesium, ammonium, or choline salts. Salt selection is now a common standard operation in the process of drug development as taught by H. Stahl and C. G Wermuth in their handbook [9].

The term "prodrug" as used herein refers to any functional derivatives (or precursors) of an API of the present invention, which, when administered to a biological system, generates said API as a result of e.g., spontaneous chemical reaction(s), enzyme catalysed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [10-13]. Furthermore, the preparation of prodrugs may be performed by conventional methods known by those skilled in the art. Methods which can be used to synthesize other prodrugs are described in numerous reviews on the subject [11,14-18]. For example, arbaclofen placarbil, listed in ChemID plus Advance database (website: chem.sis.nlm.nih.gov/chemidplus/), is a well-known prodrug of baclofen [19,20] which could be used instead of baclofen in compositions of the invention. Specific examples of other prodrugs of baclofen are given in Hanafi et al, 2011 [21], particularly baclofen esters and baclofen ester carbamates. Other prodrugs of baclofen can be found in the following patent applications: WO2010/102071, US2009197958, WO2009/096985, WO2009/061934, WO2008/086492, US2009216037, WO2005/066122, US2011021571, WO2003/077902 and WO2010/120370.

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [22,23] available online (http://www.ebi.ac.uk/thornton-srv/software/SMSD/). The term "derivative" also encompasses any metabolite of said APIs, i.e. modified or processed drug that retains at least part of the activity of the parent drug.

Particularly preferred APIs are (RS) baclofen, D-sorbitol and naltrexone HCl.

Buffer

As indicated, the pharmaceutical compositions of the invention combine APIs in a suitable buffer. The inventors have indeed found particular buffer conditions which make it possible to combine in a single, oral solution, three distinct APIs in highly different concentrations, while preserving stability and safety thereof. More particularly, the invention shows that a suitable buffer shall have a pH comprised between 4 and 7, more preferably between 4 and 6, even more preferably between 4.5 and 5.5. Furthermore, the inventors have surprisingly found that a good stability and a homogeneous solution can be obtained when the ingredients are formulated in an acetate or citrate buffer. Most remarkably, such formulations are less prone to microbial contamination (such as bacterial contamination), even in the absence of a preservative.

In this regard, a preferred object of the invention relates to a pharmaceutical composition in the form of a liquid solution, suitable for oral intake, which comprises:
 baclofen, sorbitol and naltrexone,
 a citrate or acetate buffer solution having a pH comprised between 4 and 7, and
 optionally, a preservative and/or a flavoring agent.

As exemplified in the experimental section, the liquid solutions of the invention allow maintaining the stability of the APIs in accordance with the guidance of the main national health authorities. The liquid formulations of the invention allow a homogeneous dispersion of the APIs, are not prone to microbial contamination, and show a good stability for each of the APIs.

In a preferred embodiment, the selected acetate or citrate buffer has a pH of or comprised between 4.5 and 5.5.

In a more preferred embodiment, the selected acetate or citrate buffer has a pH of about 5.5.

Surprisingly, the experimental results show that acetate or citrate buffers, as compared to other buffers (e.g., phosphate) confer high stability, no or low contamination, and highly homogeneous liquid formulations of the three APIs. The compositions of the invention, particularly with acetate buffer, are highly stable and resistant to microbial contamination, even in the absence of a preservative. More particularly, inventors have also observed that there is no need for any preservative for solutions comprising acetate buffer as a vehicle to satisfy stability conditions.

In this regard, a particular object of the invention relates to a pharmaceutical composition in the form of a liquid solution, suitable for oral intake, which comprises:
 baclofen, sorbitol and naltrexone,
 an acetate buffer solution having a pH comprised between 4 and 7, preferably between 4.5 and 5.5, and
 optionally, a flavoring agent.

Typically, such a composition is devoid of a preservative. More preferably, such a composition is devoid of a parahydroxybenzoate (paraben) compound.

Consequently, in a particular embodiment, such composition is particularly suitable for use in children.

In another particular embodiment, such a paraben free composition is packaged in unit doses. Such unit dosage form comprises 1, ½, ⅓ or ¼ of the daily therapeutic dose of the composition. In a preferred embodiment, the unit dosage form comprises half the daily therapeutic dose.

The components of the compositions may be used at different concentrations or relative ratios, which may be adjusted by the skilled person.

In an embodiment, baclofen and naltrexone are present in a relative weight ratio baclofen/naltrexone comprised between 2 and 20, preferably between 5 and 10 and more preferably of about 8.6.

In a preferred embodiment, sorbitol and naltrexone are present in a relative weight ratio sorbitol/naltrexone comprised between 100 and 500, preferably comprised between 200 and 400, more preferably of about 300.

In a preferred embodiment, baclofen, sorbitol and naltrexone are present in the solution in a relative weight ratio baclofen/sorbitol/naltrexone of x/y/1, with x being comprised between 2 and 20, preferably between 5 and 10 and more preferably of about 8.6, and y being comprised between 100 and 500, preferably comprised between 200 and 400, more preferably of about 300.

In this regard, an object of the invention is a pharmaceutical composition in the form of a solution comprising baclofen, sorbitol and naltrexone in a relative weight ratio baclofen/sorbitol/naltrexone of x/y/1, with x being comprised between 2 and 20, preferably between 5 and 10 and more preferably of about 8.6, and y being comprised between 100 and 500, preferably comprised between 200 and 400, more preferably of about 300.

In another embodiment, naltrexone is present in the solution at a final concentration comprised between 1 and 200 µg/mL, preferably between 10 and 100 µg/mL.

In a particular embodiment, naltrexone concentration is about 7 µg/mL.

In another particular embodiment, naltrexone concentration is about 14 µg/mL.

Compositions based on such low doses (i.e. naltrexone concentration equal to about 7 or 14 µg/mL) are of particular interest for the pediatric use. Thus, in a particular embodiment, such compositions are particularly suitable for pediatric formulation.

In a preferred embodiment, naltrexone concentration is about 70 µg/mL.

In another preferred embodiment, naltrexone concentration is about 140 µg/mL.

In a particular embodiment, concentration of the vehicle, e.g. citrate or acetate buffer, of the solutions according the invention is 0.2 M.

In a more particular embodiment, a solution according to the invention is free of any paraben compound and comprises:
  baclofen, sorbitol and naltrexone as active ingredients in a relative weight ratio of about 8.6/300/1 respectively, and
  an acetate buffer as a vehicle at a pH of about 5.5, and optionally, a flavoring agent.

Such compositions are particularly advantageous since, despite the lack of scientific evidence about any potential toxicity of parabens, paraben-free compositions are preferred.

Preservatives

Depending on the dosage and/or pH and/or nature of the buffer, it may be desirable to add to the composition a preservative, to further increase the stability thereof.

Preservatives may be selected from pharmaceutically-acceptable preservatives such as parabens, ascorbic acid, ascorbyl palmitate, benzoic acid, butylated hydroxyanisole, butylated hydroxytoluene, calcium ascorbate, calcium propionate, calcium sorbate, caprylic acid, dilauryl thiodipropionate, erythorbic acid, gum guaiac, glutathione, potassium bisulfite, potassium metabisulfite, potassium sorbate, propionic acid, propyl gallate, sodium ascorbate, sodium benzoate, sodium bisulfite, sodium metabisulfite, sodium propionate, sodium sorbate, sodium sulfite, sorbic acid, stannous chloride, sulfur dioxide, thiodipropionic acid, and/or tocopherols.

Accordingly, in an embodiment, the invention relates to a solution comprising:
  baclofen, sorbitol and naltrexone as active ingredients,
  a citrate or acetate buffer with a pH of or comprised between 4 and 7, preferably a pH of or comprised between 4.5 to 5.5, and
  at least one preservative.

More particularly, the addition of at least one paraben compound has been proved efficient in impeding microbial growth which is particularly advantageous for a liquid oral formulation. The at least one paraben compound can be chosen from benzylparaben, butylparaben, ethylparaben, isobutylparaben, isopropylparaben, methylparaben, propylparaben, or any of their salt. Sodium methylparaben and sodium propylparaben are particularly preferred.

Accordingly, in an embodiment, the invention relates to a solution comprising:
  baclofen, sorbitol and naltrexone as active ingredients,
  a citrate buffer with a pH of or comprised between 4 and 7, preferably a pH of or comprised between 4.5 to 5.5, and
  at least one paraben.

In another embodiment, the invention relates to a solution comprising:
  baclofen, sorbitol and naltrexone as active ingredients,
  an acetate buffer with a pH of or comprised between 4 and 7, preferably a pH of or comprised between 4.5 to 5.5, and
  at least one paraben.

In a particular embodiment, the at least one paraben compound is a methyl paraben and/or a propyl paraben. In a more particular embodiment, the at least one paraben compound is sodium methyl paraben and/or sodium propyl paraben. The sodium methyl paraben and/or sodium propyl paraben may be used in a concentration of about 0.18% w/v and about 0.02% w/v, respectively. As exemplified in experimental section, the inventors have found stable solutions in which APIs are not prone to degradation at paraben concentrations far below the safe doses according to the European Medicines Agency guidelines, i.e. 166 mg/day for methyl paraben and 50 mg/day for propyl paraben [24]. This is of particular interest for use in children or in lifelong/chronic treatments.

Then, in an embodiment, the doses of methyl paraben and propyl paraben are less than 166 and 50 mg/day, respectively.

In a preferred embodiment, the doses of methyl and propyl parabens are less than 80 and 25 mg/day, respectively.

In a more preferred embodiment, doses of methyl and propyl parabens are about 18 and 2 mg/day.

In an even more preferred embodiment, compositions of the invention are free of parabens.

Flavoring Agent

In a particular embodiment, the compositions of the invention further contain at least one flavor or flavoring agent. Such agents can mask the taste of the APIs and/or other compounds such as buffer, and facilitate oral intake. Flavoring agents can be either extracted from natural sources, such as essential oils from flowers, fruits or roots, or artificially synthesized. A large variety of pharmaceutically-acceptable flavoring agents can be used. Preferred flavoring agents are not interfering with the quantification of APIs, and not disrupting the stability of the formulations of the invention. The flavor should be adjusted as a function of its ability to mask the unpalatable taste. Flavoring agents may be selected from pharmaceutically acceptable flavors such as vanillin, isoamyl acetate, acetaldehyde, acetoin, aconitic acid, anethole, benzaldehyde, N-butyric acid, D- or L-carvone cinnamaldehyde, citral, decanal, diacetyl, ethyl acetate, ethyl butyrate, ethyl vanillin, eugenol, geraniol, geranyl acetate, glycerol tributyrate limonene, linalool, linalyl acetate, 1-malic acid, methyl anthranilate, 3-methyl-3-phenyl glycidic acid, ethyl ester, or piperonal. Preferred flavoring agents are vanillin or isoamyl acetate (banana oil).

A preferred solution according to the invention thus comprises:
baclofen, sorbitol and naltrexone as active ingredients,
an acetate or citrate buffer as a vehicle with a pH of or comprised between 4 and 7, and more preferably of or comprised between 4.5 and 5.5,
optionally at least one preservative, and
a flavoring agent, preferably selected from vanillin or isoamyl acetate.

When using acetate buffer as a vehicle, isoamyl acetate is particularly preferred. Preferred concentration for isoamyl acetate is between 0.1 to 2.0 mg/mL, and more preferably of about 0.4 mg/mL.

Consequently, a more preferred solution according to the invention comprises:
baclofen, sorbitol and naltrexone as active ingredients, preferably in a relative weight ratio of about 8.6/300/1 respectively,
acetate buffer as a vehicle with a pH comprised between 4 and 7, preferably between 4.5 and 5.5, and
isoamyl acetate, preferably at a concentration comprised between 0.1 and 2.0 mg/mL.

Specific examples of compositions of the invention are detailed in table 2 below.

TABLE 2

| Ingredients per 1 mL of composition n° | N° 1 | N° 2 | N° 3 | N° 4 | N° 5 | N° 6 |
|---|---|---|---|---|---|---|
| D-sorbitol (mg) | 4.2 | 4.2 | 21 | 21 | 42 | 42 |
| Naltrexone HCl (mg) | 0.014 | 0.014 | 0.07 | 0.07 | 0.14 | 0.14 |
| RS baclofen (mg) | 0.12 | 0.12 | 0.6 | 0.6 | 1.2 | 1.2 |
| Acetate buffer pH 5.5 | | | to 1 mL | | | |
| Sodium methyl paraben (mg) | 1.8 | — | 1.8 | — | 1.8 | — |
| Sodium propyl paraben (mg) | 0.2 | — | 0.2 | — | 0.2 | — |
| Isoamyl acetate (banana oil) (mg) | 0.4 | 0.4 | 0.4 | 0.4 | 0.4 | 0.4 |

Further Compounds

Additional compounds which are compatible with oral pharmaceutical formulations can be added to the formulation of the invention as needs identified by the one skilled in the art. It can be, for example, at least one other compatible drug or dietary supplement, other compatible excipient, as sugar or sweetener, coloring agent, antioxidant, viscosity modifier, flavor enhancer, co-solvent or preservative.

For example sweeteners or sugars can be chosen from: dextrose, glycerine, maltitol, *stevia*, aspartame, sucralose, neotame, acesulfame potassium, and/or saccharin. Depending of the amount of sugar added to the solution, a syrup can be obtained that might be considered as an advantageous formulation in the case where the solution is specifically formulated for children.

Examples of coloring agents are E 102 (Tartazine), E 103 (Chrysoine S), E 104 (Quinoline Yellow), E 105 (Fast Yellow AB), E 110 (Orange Yellow S, Sunset Yellow FCF), E 111 (Orange GGN), E 120 (Cochineal, carminic acid), E 122 (Azorubin, Carmoisine), E 123 (Amaranth), E 124 (Cochineal Red A, Ponceau 4 R), E 125 (Scarlet GN), E 126 (Ponceau 6 R), E 131 (Patent Blue V), E 132 (Indigotin indigo carmine), E 141 (Copper complexes of chlorophylls and chlorophyllins), E 151 (Brilliant Black BN, Black PN), E 152 (Black 7984), E 153 (*Carbo medicinalis vegetalis* (charcoal)), E 160 (a), (Alpha-, Beta-, Gamma-Carotene), E 160 (b) (Bixin and Norbixin (Roucou, Annatto)), E 162 (Beetroot red, betanin), E 171 (Titanium dioxide), E 172 (Iron oxides and hydroxides), or E 181 (Burnt umber).

In an embodiment, the invention relates to method for preparing one of the above compositions, comprising providing baclofen, sorbitol and naltrexone and admixing said active ingredients in solution in a citrate or acetate buffer having a pH comprised between 4 and 7. The method may further comprise adding to the solution one or more further agents such as, in particular, a preservative and/or a flavoring agent. The compositions may also further comprise additional active agents.

A particular method for preparing a composition of the invention comprises the steps of:
i) preparing a solution by:
dispensing about 20% of the desired final volume of acetate buffer (e.g., 0.17 M),
then dissolving sodium methyl paraben and sodium propyl paraben,
then heating to 45-55° C., preferably about 50° C., with stirring until dissolving,
then cooling to about 25-35, typically about 30° C.;
ii) preparing another solution by:
dispensing about 70% of the desired final volume of acetate buffer (e.g., 0.17 M),
then adding sorbitol, naltrexone and baclofen,
then mixing until dissolving;
iii) mixing the solutions obtained in step i) and ii), preferably under gentle agitation for 5 minutes,
iv) adding a flavoring agent (e.g., banana flavor) to the solution obtained in step iii) and mixing until dissolving,
v) if needed, adjusting pH to 5.4-5.6 with 50% w/w NaOH solution or glacial acetic acid (>99.0%), and
vi) making up to the final volume with acetate buffer (e.g., 0.17 M).

Another suitable method for preparing a composition of the invention comprises the steps of:
i) dispensing about 90% water of the total batch sized required,
ii) optionally adding sodium methyl paraben and sodium propyl paraben, then mixing until dissolving,
iii) adding sodium acetate trihydrate and glacial acetic acid, then mixing until dissolving,
iv) adding sorbitol, naltrexone and baclofen,
v) adding isoamyl acetate, then mixing until dissolving,
vi) if needed, adjusting pH to 5.4-5.6 with a 50% w/w NaOH solution or glacial acetic acid (>99.0%), and
vii) making up weight with water.

The composition may be packaged in any suitable device or container, such as a flask, bottle, glass or plastic unit-dose container such as stick-pack, tube, ampoule, etc., typically under sterile conditions. More commonly the pharmaceutical formulations of the invention are prescribed to the patient in "patient packs" containing a number dosing units or other means for administration of metered unit doses for use during a distinct treatment period in a single package, usually a blister pack. The inclusion of a package insert has been shown to improve patient compliance with the physician's instructions. The patient packs encompass sets of single-dose sachets or ampoules containing the suitable amount of the liquid formulation as disclosed herein.

Alternatively, they can be supplied in a larger container as a bottle, then the invention also relates to pharmaceutical kit of parts comprising a bottle containing any liquid formulation as disclosed herein, a cap and/or a pipette or a pipette-cap system, and optionally instructions.

The bottle can be made of any material convenient with the storage and the use requirements comprising polymers, metal and glass and so on. It is of importance that the bottle material does not interfere with the components of the liquid formulation as disclosed herein. In an embodiment it is made of glass. In order to protect the APIs from light-induced degradation, a preferred embodiment comprises amber glass bottle.

The bottle capacity can be adapted to the volume to be administrated for the period during which the liquid formulation as disclosed herein is stable. For instance, a solution which is stable for 10 days after opening associated to an administration of two doses of 5 mL per day may be stored into bottle of about 100 mL. The one skilled in the art will easily adapt the volume of the bottle to that needed as previously suggested.

The pipette is made of glass, plastic or any material convenient with the use and the storage of the liquid solutions as disclosed herein. The pipette may be graduated to facilitate the administration of the liquid solution. In an embodiment, the pipette is a 5 mL graduated pipette.

The cap (or closure) is any article for closing a suitably shaped opening. It encompasses, but is not limited to, childproof closures, waterproof closures, pipette-associated caps, solid caps, plastic or polymeric caps. In an embodiment, the cap is screwed on the bottle top or interlocked with the top of the bottle.

A sealing element may be required for the tightness of the system bottle-cap or bottle-pipette-cap or bottle-pipette or pipette-cap. This element can be supplied on its own and further fit in the bottle-neck, or around the pipette, or in the cap, or it can be previously adapted to the bottle, the cap or the pipette.

The invention also relates to a kit of parts comprising a package containing four bottles of the liquid formulation as disclosed herein and four pipettes intended to remove the needed amount of the liquid formulation and/or instructions.

In another aspect, the invention relates to a kit of parts allowing the extemporaneously preparation of the solutions according to the invention.

In a preferred aspect, the invention relates to a kit of parts comprising several unit-doses such as ampoules, stick-packs, tubes, etc. These unit-doses are of particular interest for repeated administration. Such unit dosage form comprises 1, ½, ⅓ or ¼ of the daily therapeutic dose of the composition. In another embodiment, the unit dosage form comprises half the daily therapeutic dose of the composition.

The pharmaceutical compositions of the invention may be used in mammalian subjects, particularly human subjects, for treating any disease for which this combination is efficient, particularly nervous system diseases (e.g., CMT (particularly CMT1A), neuropathic pain, drug or alcohol withdrawal, and Parkinson's disease). They are more particularly suitable for treating CMT.

Consequently, in an embodiment, the invention also relates to a composition of the invention for use for treating CMT.

The invention also relates to a method for treating nervous system diseases (e.g. CMT, neuropathic pain, drug or alcohol withdrawal, Parkinson's disease, . . . ), and more particularly to a method for treating CMT in a subject in need thereof, comprising administering to said subject an effective amount of a composition of the invention.

Further aspects and advantages of the invention will be disclosed in the following experimental section, which is illustrative of the invention.

Examples

I. Solution as a Dosage Form

The use of both a solution and a solid suspension in a capsule formulation has been considered. This latter dosage form is based on the use of a carrier excipient which is solid below 40° C., and in molten state at around 55° C. Thus it could be considered as a dosage form of choice in order to ensure a homogeneous dispersion of naltrexone (the active principle present in the lowest quantity in the medication). D-alpha-tocopheryl polyethylene glycol 1000 succinate (VETPGS) has been chosen as carrier because it is a widely used and well characterized GRAS excipient.

Stability of the compounds in the solution or suspension was assessed by measuring the remaining concentration of the APIs or the apparition of degradation products after one week at 25° C. Surprisingly, in the semi-solid formulation, baclofen concentration dropped of around 14% whereas impurity A (the main degradation product of baclofen) increased by 75% over one week at 25° C., thereby showing substantial temperature- and time-dependent degradation of baclofen in semi-solid formulation, while the APIs were stable in the solution. The results are summarized in table 3 below.

TABLE 3

Stability of compounds

| Compounds | Solution | Capsule (semi-solid) |
|---|---|---|
| Baclofen | + | − |
| Sorbitol | + | + |
| Naltrexone | + | + |
| Propyl parabens | + | N/A |

+ stability characteristics in accordance with the European Pharmacopeia specifications;
− stability characteristics do not meet stability requirement of European Pharmacopeia specifications;
N/A Not Available.

These results have been confirmed by stability assays performed for one week at 50° C. which is considered as indicative for long term stability of compounds according the pharmacopeial guidance.

II. Preparation and Physicochemical Properties of Solutions of the Invention

Tables 4.A and 4.B below show compositions in the form of solutions that have been prepared (volume adjusted to 100 mL with the buffer):

TABLE 4.A

| | Composition number | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Sorbitol (% w/w) | 0.21 | 0.21 | 0.21 | 0.21 | 0.21 | 0.21 | 0.21 | 0.21 | 0.21 | 0.21 | 0.21 | 0.21 | 2.1 |
| Naltrexone (% w/w) | 7E−04 | 7E−04 | 7E−04 | 7E−04 | 7E−04 | 7E−04 | 7E−04 | 7E−04 | 7E−04 | 7E−04 | 7E−04 | 7E−04 | 0.007 |
| Baclofen (% w/w) | 0.006 | 0.006 | 0.006 | 0.006 | 0.006 | 0.006 | 0.006 | 0.006 | 0.006 | 0.006 | 0.006 | 0.006 | 0.06 |
| Acetate buffer 0.2M | pH 4.5 | pH 5 | pH 5.5 | / | / | / | / | / | / | pH 5 | / | / | pH 5.5 |
| Phosphate buffer¥ | / | / | / | pH 4.5 | pH 5 | pH 5.5 | / | / | / | / | pH 5 | / | / |
| Citrate buffer 0.2M | / | / | / | / | / | / | pH 4.5 | pH 5 | pH 5.5 | / | / | pH 5 | / |
| Sodium methyl paraben (% w/v) | / | / | / | / | / | / | / | / | / | 0.18 | 0.18 | 0.18 | 0.18 |
| Sodium propyl paraben (% w/v) | / | / | / | / | / | / | / | / | / | 0.02 | 0.02 | 0.02 | 0.02 |

¥0.01M potassium dihydrogen orthophosphate-0.05M di-sodium hydrogen orthophosphate
% w/w: mass in g for 100 g of the final composition
% w/v: mass in g for 100 mL of the final composition

TABLE 4.B

| | Composition number | |
|---|---|---|
| | 14 | 15 |
| Sorbitol (% w/w) | 4.2 | 4.2 |
| Naltrexone (% w/w) | 0.014 | 0.014 |
| Baclofen (% w/w) | 0.12 | 0.12 |
| Acetate buffer 0.2 M | pH 5.5 | pH 5.0 |
| Sodium methyl paraben (% w/v) | 0.18 | 0.18 |
| Sodium propyl paraben (% w/v) | 0.02 | 0.02 |
| Isoamyl acetate (banana flavor) (% w/v) | 0.04 | 0.04 |

% w/w mass in g for 100 g of the final composition
% w/v mass in g for 100 mL of the final composition The stability of these compositions under various conditions was tested. As shown below, the solutions of the present invention have been found stable in a number of tests. For instance, they have remained clear and stable, without precipitation or degradation of the active ingredients (cf. chemical stability results, below). Moreover, the solutions have been subjected to alternating refrigeration and room temperature conditions, without noticing any change in the appearance and stability of the solution.

A. Chemical Stability/Microbial Growth

Different formulations have been tested for their stability: changes in terms of pH, appearance and coloration were checked over one month at 5° C., 25° C. and 40° C. at one week intervals (data summarized in table 5.A). Both citrate and acetate buffered solutions were stable in terms of pH, coloration and appearance (table 5.A), phosphate buffered solutions as well. The initial observation of 1 week time point confirms that pH, color and appearance of the solutions no 14 and 15 were stable under 25° C., 40° C. and a 5-40° C. 24 hour temperature cycling. Solutions no 14 and 15 were further not prone to changes in baclofen, naltrexone or sorbitol contents under each condition investigated (table 5.B). The best stability was observed with a pH 5.5 acetate buffer. In terms of API degradation, citrate and acetate buffered solutions were very stable, even in the absence of preservative. Phosphate buffered formulations were found prone to microbial contamination; citrate buffered solutions, though in a less extent, also did in the absence of a preservative (table 6).

Regarding chemical stability of the APIs, a formulation was considered stable when the API concentration decreased by less than 5% after 4 weeks at 25° C. (table 5.A). Solutions comprising acetate buffer as vehicle (no 1-3) have shown the best stability. A reduction in baclofen content was observed in formulations using phosphate buffer as vehicle, especially for the solution no 5 wherein a fall of 40% (reported to the initial concentration) in baclofen content is observed. A reduction in naltrexone concentration was observed in the solution no 5 (phosphate buffered, pH 5.0). A reduction in sorbitol concentration was also observed in phosphate buffered solutions (no 4 and 6).

It appears thus that acetate and citrate buffers are the best vehicle in term of stability of the solutions and of chemical stability of the APIs. It is noteworthy that acetate buffered solutions are not prone to microbial contamination (table 6).

TABLE 5.A

| | Solution Number | | | | | | | | |
|---|---|---|---|---|---|---|---|---|---|
| | 1 | 2 | 3 | 4 | 5 | 6 | 7 | 8 | 9 |
| pH, color, appearance (5° C., 25° C., 40° C.) | +++ | +++ | +++ | + | + | + | ++ | ++ | ++ |

TABLE 5.A-continued

|  |  |  | Solution Number | | | | | | | | |
|---|---|---|---|---|---|---|---|---|---|---|---|
|  |  |  | 1 | 2 | 3 | 4 | 5 | 6 | 7 | 8 | 9 |
| API degradation (4 weeks at 40° C.) | Baclofen (% nominal) | Initial | 95.5 | 98.1 | 97.5 | 93 | 89.3 | 98.7 | 97.5 | 98.4 | 97.9 |
|  |  | Recovery | 96.0 | 98.5 | 96.4 | 84.5 | 52.4 | 92.7 | 93.6 | 96.0 | 98.4 |
|  | Naltrexone (% nominal) | Initial | 94.0 | 95.9 | 97.1 | 84.3 | 82.9 | N/A | 91.8 | 91.1 | N/A |
|  |  | Recovery | 93.0 | 95.5 | 95.7 | 86.9 | 58.4 | N/A | 91.4 | 91.7 | N/A |
|  | Sorbitol (% nominal) | Initial | 95.2 | 99.0 | 97.1 | 95.7 | 95.7 | 91.9 | 97.1 | 98.1 | 97.1 |
|  |  | Recovery | 96.7 | 99.5 | 98.6 | 80.0 | 94.3 | 79.5 | 98.1 | 96.2 | 95.7 |

+++, ++ and +: satisfaction score (in a decreasing order)
N/A: not available

TABLE 5.B

|  | Results (mg/mL) | | | | | |
|---|---|---|---|---|---|---|
|  | baclofen | | naltrexone | | sorbitol | |
| Solution n° | 14 | 15 | 14 | 15 | 14 | 15 |
| Initial | 1.18 | 1.20 | 0.132 | 0.134 | 41.5 | 41.2 |
| 25° C. (1 week) | 1.19 | 1.18 | 0.130 | 0.132 | 41.2 | 41.2 |
| 40° C. (1 week) | 1.19 | 1.19 | 0.131 | 0.133 | 41.9 | 41.6 |
| 5-40° C. (1 week temperature cycling) | 1.20 | 1.18 | 0.131 | 0.131 | 42.0 | 41.5 |

TABLE 6

| Storage temperature | Microbial contamination Solution number | | | | | | | | |
|---|---|---|---|---|---|---|---|---|---|
| (4 weeks) | 1 | 2 | 3 | 4 | 5 | 6 | 7 | 8 | 9 |
| 5° C. | no | no | no | +++ | +++ | +++ | ++ | ++ | ++ |
| 25° C. | no | no | no | +++ | +++ | +++ | ++ | ++ | ++ |
| 40° C. | no | no | no | +++ | +++ | +++ | ++ | ++ | no | no: no microbial contamination
++ and +++: mid and high microbial contamination, respectively Several preservatives have been tested (for example propylene glycol or parabens) to further increase stability, especially for citrate compositions. The use of parabens (sodium methyl paraben and sodium propyl paraben, table 7) has been found to lead to citrate based solutions resistant to microbial contamination. In contrast, phosphate buffer based solutions could not be stabilized, nor avoid microbial contamination, even in the presence of preservatives (tables 6 and 7).

TABLE 7

|  | Solution Number | | | | | |
|---|---|---|---|---|---|---|
|  | 2 | 5 | 8 | 10 | 11 | 12 |
| Vehicle | acetate | phosphate | citrate | acetate | phosphate | citrate |
| Preservative(s) |  | none |  |  | parabens |  |
| Microbial contamination | no | +++ | ++ | no | ++ | no | no: no microbial contamination
++ and +++: mid and high microbial contamination, respectively B. Palatability and Compliance Palatability is particularly important when talking about oral drugs, and directly linked to the compliance of the patients, especially when treating chronic diseases. A prerequisite for flavoring agents is to not interfere with APIs and thereby hamper their stability. More specifically, they should not interfere neither with the quality and quantitative analyses of the APIs.

Several flavors have been tested. Some of them were finally discarded as interfering with the APIs and thereby impeding their further quantification. Vanillin and isoamyl acetate were tested for their palatability. Briefly, a single drop of each tested formulation was placed on the tongue of the volunteers. They were then asked to grade the palatability of the solutions from 0 (very unpalatable) to 10 (very palatable).

Isoamyl acetate containing solution obtained the best score.

C. Regulatory Requirements

All medicines have to comply with the pharmacopeial guidance which limits for the concentration of impurities in pharmaceutical products. The required criteria are defined by the ICH (International Conference on Harmonization of technical requirements for registration of pharmaceuticals for human use).

Stability of solution no 13 has been studied; it has been placed at room temperature for extended period of time according the specifications of ICH: appearance of the APIs degradation- and related-products has been assessed over 24 months for solutions stored at 25° C./60% Relative Humidity (RH).

Impurity A, that is (RS)-4-amino-3-(4-chlorophenyl) butyric acid lactam (Relative Retention Time (RRT, HPLC analysis) 0.82-0.83), is known to be generated during the synthesis process of baclofen and is known to be increased during storage of the drug as a degradation product.

Sorbitol related substances that have been searched for are mannitol (RRT 1.21-1.23) and iditol (RRT 0.88-0.89).

As shown in table 8, the product characteristics were compatible with regulatory specifications.

TABLE 8

| ICH Test | Results for 24 months 25° C./60% RH |
|---|---|
| Sorbitol stability | |
| Sorbitol quantity[¥] | passed |
| Sorbitol related substances[†] | passed |
| Baclofen stability | |
| Baclofen quantity[¥] | passed |
| Impurity A[†] | passed |
| Naltrexone stability | |
| Naltrexone quantity[¥] | passed |
| Naltrexone related substances[¥] | passed |

TABLE 8-continued

| ICH Test | Results for 24 months 25° C./60% RH |
|---|---|
| Other | |
| Parabens quantity[¥] | passed |
| pH assessment (alarm: change of 0.2 of pH unit or more) | passed |
| Microbial quality (alarm: any microbial growth) | passed |

[¥]alarm: ±5% (total area) from initial value;
[†]alarm: growth by 0.1% (total area) or more;
RH Relative Humidity.

After an initial one week observation, solutions 14 and 15 also passed existing drug product specification limits. The compositions of table 9 represent particularly advantageous embodiments of the invention.

TABLE 9

| | Formulation | |
|---|---|---|
| Material | (% w/v) | (% w/w) |
| Sodium methyl paraben | 0.180 | 0.176 |
| Sodium propyl paraben | 0.020 | 0.020 |
| D-sorbitol | 4.200 | 4.101 |
| Naltrexone HCl | 0.014 | 0.014 |
| Baclofen (RS form) | 0.120 | 0.117 |
| Isoamyl acetate (banana) flavor | 0.040 | 0.041 |
| Acetate buffer pH 5.5 | to 100 | — |
| Sodium acetate trihydrate | — | 2.221 |
| Glacial acetic acid | — | 0.241 |
| Water for injection | — | 93.070 |

% w/w mass in g for 100 g of the final composition
% w/v mass in g for 100 mL of the final composition D. Product Preparation Two improved methods were developed for the preparation of the compositions of the invention. These methods are described in FIGS. 1 and 2.

Figure 1:
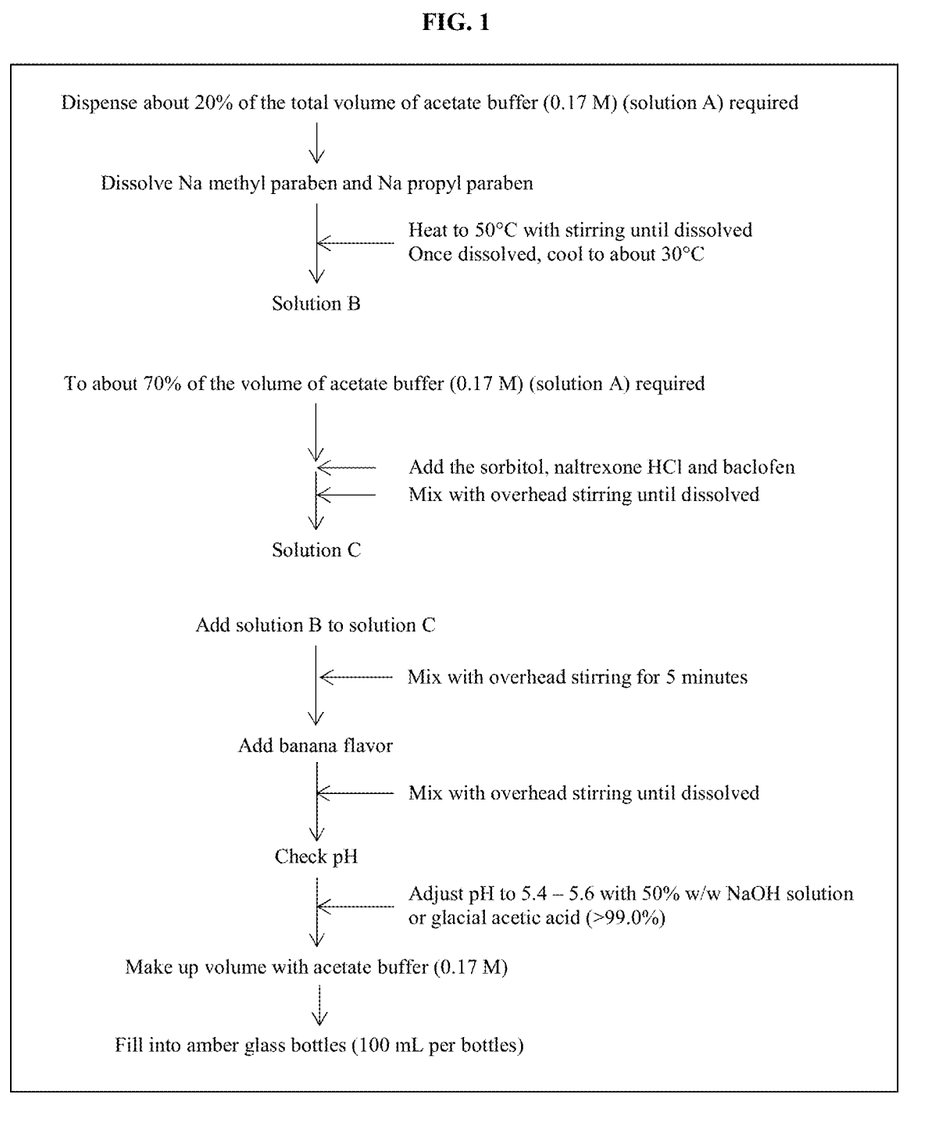
FIG. 1 is a chart describing a first method of manufacture of the compositions of the invention.
Figure 2:
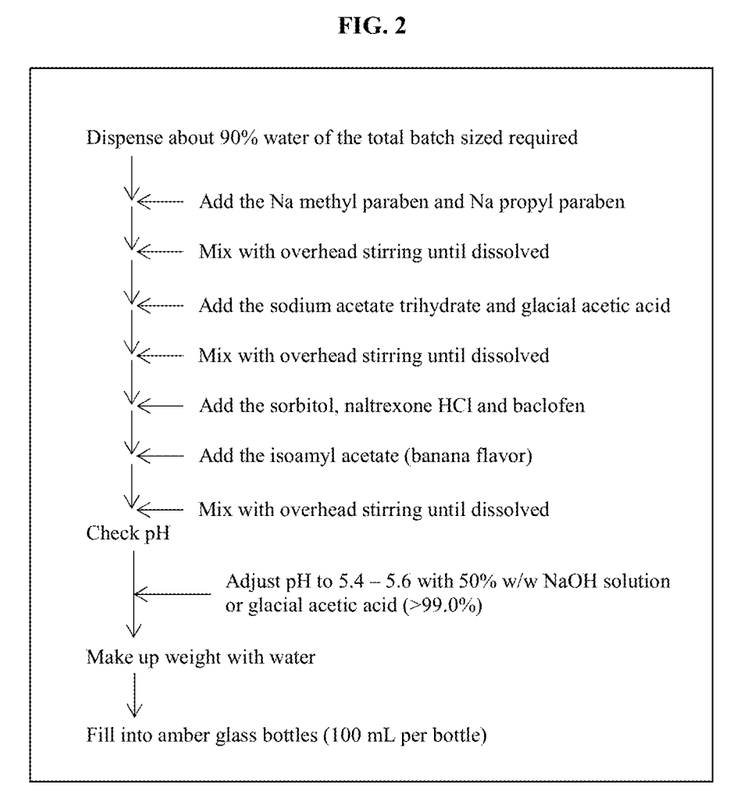
FIG. 2 is a chart describing another method of the batch manufacture of the compositions of the invention.

The diagram shown in FIG. 1 provides a first method of manufacture of the compositions of the invention.

The second diagram (shown in FIG. 2) provides another method of the batch manufacture of the compositions of the invention. This method presents the particular advantage of comprising less steps, and further not necessitates an initial heating step.

Compositions obtained by these methods respond to the pressing need for formulations that combine APIs with high difference in concentrations in a stable form, optionally paraben-free, that can be of particular interest for children and people constrained to take de medicament lifelong. Use of glass bottles with graduate pipette or of unit-dosage packs is of great interest since it improves the compliance in lifelong/chronic invalidating diseases such as Charcot-Marie-Tooth disease.

BIBLIOGRAPHY

1 Gerber U & Gahwiler B H (1994) GABAB and adenosine receptors mediate enhancement of the K+ current, IAHP, by reducing adenylyl cyclase activity in rat CA3 hippocampal neurons. *J. Neurophysiol.* 72, 2360-7.
2 Oka K, Yamamoto M, Nonaka T & Tomonaga M (1996) The significance of artificial cerebrospinal fluid as perfusate and endoneurosurgery. *Neurosurgery* 38, 733-6.
3 Avellino A M & Loeser J D (2000) Intrathecal baclofen for the treatment of intractable spasticity of spine or brain etiology. *Neuromodulation* 3, 75-81.
4 Keast R S J, Canty T M & Breslin P A S (2004) Oral zinc sulfate solutions inhibit sweet taste perception. *Chem. Senses* 29, 513-21.
5 Maisel N C, Blodgett J C, Wilbourne P L, Humphreys K & Finney J W (2013) Meta-analysis of naltrexone and acamprosate for treating alcohol use disorders: when are these medications most helpful? *Addiction* 108, 275-293.
6 Friedmann P D, Mello D, Lonergan S, Bourgault C & O'Toole T P (2013) Aversion to injection limits acceptability of extended-release naltrexone among homeless, alcohol-dependent patients. *Subst. Abus.* 34, 94-96.
7 Hulse G K, Morris N, Arnold-Reed D & Tait R J (2009) Improving clinical outcomes in treating heroin dependence: randomized, controlled trial of oral or implant naltrexone. *Arch. Gen. Psychiatry* 66, 1108-1115.
8 Hulse G K & Basso M R (2000) The association between naltrexone compliance and daily supervision. *Drug Alcohol Rev.* 19, 41-48.
9 Stahl P H & Wermuth C G (2008) *Pharmaceutical Salts* Wiley.
10 Ettmayer P, Amidon G L, Clement B & Testa B (2004) Lessons learned from marketed and investigational prodrugs. *J. Med. Chem.* 47, 2393-404.
11 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.
12 Heimbach T, Oh D M, Li L Y, Rodriguez-Hornedo N, Garcia G & Fleisher D (2003) Enzyme-mediated precipitation of parent drugs from their phosphate prodrugs. *Int. J. Pharm.* 261, 81-92.
13 Steffansen B, Nielsen C U, Brodin B, Eriksson A H, Andersen R & Frokjaer S (2004) Intestinal solute carriers: an overview of trends and strategies for improving oral drug absorption. *Eur. J. Pharm. Sci.* 21, 3-16.
14 Stella V J (2007) *Prodrugs: challenges and rewards.* (A. Press and Springer, eds.) Springer Singapore Pte. Limited, New-York.
15 Stella V J (2004) Prodrugs as therapeutics. *Expert Opin. Ther. Pat.* 14, 277-280.
16 Stella V J & Nti-Addae K W (2007) Prodrug strategies to overcome poor water solubility. *Adv. Drug Deliv. Rev.* 59, 677-94.
17 Higuchi T & Stella V J (1975) *Pro-drugs as Novel Drug Delivery System*, ACS Sympos American Chemical Society, Washington, D.C.
18 Roche E B (1977) *Design of biopharmaceutical properties through prodrugs and analogs: a symposium*, American P The Academy, Washington, D.C.
19 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.
20 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.
21 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.

22 Leach A R & Gillet V J *An Introduction to Chemoinformatics* (Springer-Verlag New York Inc, ed.).
23 Rahman S A, Bashton M, Holliday G L, Schrader R & Thornton J M (2009) Small Molecule Subgraph Detector (SMSD) toolkit. *J. Cheminform.* 1, 12.
24 Committee for Medicinal Products for Human (2013) *Reflection paper on the use of methyl-and propylparaben as excipients in human medicinal products for oral use.* EMA/CHMP/SWP/272921/2012.

We claim:

1. A pharmaceutical composition comprising, in the form of a solution:
    baclofen or a pharmaceutically acceptable salt thereof, sorbitol or a pharmaceutically acceptable salt thereof, and naltrexone or a pharmaceutically acceptable salt thereof as active ingredients, and
    an acetate or citrate buffer, or a combination thereof;
wherein the solution has a pH of between about 4 and about 7.

2. The composition of claim 1, comprising naltrexone or a pharmaceutically acceptable salt thereof in an amount between about 1 and about 200 µg/mL.

3. The composition of claim 2, comprising naltrexone or a pharmaceutically acceptable salt thereof in an amount between about 10 and about 100 µg/mL.

4. The composition of claim 2, wherein naltrexone or a pharmaceutically acceptable salt thereof is in an amount of about 70 µg/mL.

5. The composition of claim 2, comprising naltrexone or a pharmaceutically acceptable salt thereof in an amount of about 140 µg/mL.

6. The composition of claim 1, wherein baclofen or a pharmaceutically acceptable salt thereof, sorbitol or a pharmaceutically acceptable salt thereof, and naltrexone or a pharmaceutically acceptable salt thereof are present in a relative weight ratio of about 8.6/300/1.

7. The composition of claim 1, comprising:
    sorbitol, or a pharmaceutically acceptable salt thereof, in an amount of about 4.2 mg/mL,
    naltrexone, or a pharmaceutically acceptable salt thereof, in an amount of about 0.014 mg/mL, and
    baclofen, or a pharmaceutically acceptable salt thereof, in an amount of about 0.12 mg/mL.

8. The composition of claim 1, comprising:
    sorbitol, or a pharmaceutically acceptable salt thereof, in an amount of about 21 mg/mL,
    naltrexone, or a pharmaceutically acceptable salt thereof, in an amount of about 0.07 mg/mL, and
    baclofen, or a pharmaceutically acceptable salt thereof, in an amount of about 0.6 mg/mL.

9. The composition of claim 1, comprising:
    sorbitol, or a pharmaceutically acceptable salt thereof, in an amount of about 42 mg/mL,
    naltrexone, or a pharmaceutically acceptable salt thereof, in an amount of about 0.14 mg/mL, and
    baclofen, or a pharmaceutically acceptable salt thereof, in an amount of about 1.2 mg/mL.

10. The composition of claim 1, further comprising at least one flavoring agent.

11. The composition of claim 10, wherein the at least one flavoring agent is isoamyl acetate.

12. The composition of claim 11, comprising isoamyl acetate in an amount between about 0.1 and about 2.0 mg/mL.

13. The composition of claim 12, comprising isoamyl acetate in an amount of about 0.4 mg/mL.

14. The composition of claim 1, further comprising at least one preservative.

15. The composition of claim 14, wherein the at least one preservative is a paraben.

16. The composition of claim 15, wherein the at least one preservative is methyl paraben, propyl paraben, or a combination thereof.

17. The composition of claim 16, comprising methyl paraben in a concentration of about 0.18 g per 100 mL or propyl paraben in a concentration of about 0.02 g per 100 mL of the composition, respectively; or a combination thereof.

18. A pharmaceutical composition comprising, in the form of a solution:
    sorbitol, or a pharmaceutically acceptable salt thereof, in an amount of about 4.2 mg/mL,
    naltrexone, or a pharmaceutically acceptable salt thereof, in an amount of about 0.014 mg/mL,
    baclofen, or a pharmaceutically acceptable salt thereof, in an amount of about 0.12 mg/mL,
    isoamyl acetate in an amount of about 0.4 mg/mL,
    sodium methyl paraben in an amount of about 0.18 mg/mL,
    sodium propyl paraben in an amount of about 0.02 mg/mL, and
    an acetate buffer;
wherein the solution has a pH of between 4 and 7.

19. The composition of claim 18, wherein the pH of the solution is about 5.5.

20. The composition of claim 18, wherein the acetate buffer comprises:
    sodium acetate in an amount of about 2.221 g per 100 g of the final composition;
    acetic acid in an amount of about 0.241 g per 100 g of the final composition; and
    water in an amount of about 93.070 g per 100 g of the final composition.

21. The composition of claim 1, wherein the composition is free of paraben.

22. The composition of claim 1, comprising at least one further compound selected from the group consisting of antioxidants, emulsifiers, viscosity modifiers, sweeteners, flavor enhancers, coloring agents, co-solvents, solubilizers, and combinations thereof.

23. The composition of claim 1, wherein the sorbitol or a pharmaceutically acceptable salt thereof is D-sorbitol, the baclofen or a pharmaceutically acceptable salt thereof is RS baclofen, and the naltrexone or a pharmaceutically acceptable salt thereof is naltrexone HCl.

24. The composition of claim 7, wherein the sorbitol or a pharmaceutically acceptable salt thereof is D-sorbitol, the baclofen or a pharmaceutically acceptable salt thereof is RS baclofen, and the naltrexone or a pharmaceutically acceptable salt thereof is naltrexone HCl.

25. The composition of claim 8, wherein the sorbitol or a pharmaceutically acceptable salt thereof is D-sorbitol, the baclofen or a pharmaceutically acceptable salt thereof is RS baclofen, and the naltrexone or a pharmaceutically acceptable salt thereof is naltrexone HCl.

26. The composition of claim 9, wherein the sorbitol or a pharmaceutically acceptable salt thereof is D-sorbitol, the baclofen or a pharmaceutically acceptable salt thereof is RS baclofen, and the naltrexone or a pharmaceutically acceptable salt thereof is naltrexone HCl.

27. A method for preparing the composition of claim 1, comprising the steps of providing baclofen or a pharmaceutically acceptable salt thereof, sorbitol or a pharmaceutically acceptable salt thereof, and naltrexone or a pharmaceutically acceptable salt thereof; and admixing said baclofen or a pharmaceutically acceptable salt thereof, sorbitol or a pharmaceutically acceptable salt thereof, and naltrexone or a pharmaceutically acceptable salt thereof in a citrate or acetate buffer, wherein the resulting solution has a pH between 4 and 7.

28. The method of claim 27, comprising the steps of:
   i) preparing a first solution by:
      dispensing about 20% of a desired final volume of an acetate buffer;
      then dissolving sodium methyl paraben and sodium propyl paraben;
      then heating to 45-55° C., optionally with stirring, until dissolved;
      then cooling to about 25-35° C.;
   ii) preparing a second solution by:
      dispensing about 70% of the desired final volume of acetate buffer;
      then adding sorbitol, naltrexone, and baclofen;
      then mixing until dissolved;
   iii) mixing the first and second solutions obtained in step i) and ii);
   iv) optionally, adding a flavoring agent to the solution obtained in step iii) and mixing until dissolved;
   v) if needed, adjusting pH to 5.4-5.6 with 50% w/w NaOH solution or acetic acid; and
   vi) if needed, adding sufficient acetate buffer to reach the desired final volume.

29. The method of claim 27, comprising the steps of:
   i) dispensing about 90% of an amount of water required for a total batch size;
   ii) optionally adding sodium methyl paraben and sodium propyl paraben, then mixing until dissolved;
   iii) adding sodium acetate and acetic acid, then mixing until dissolved;
   iv) adding sorbitol, naltrexone and baclofen;
   v) adding isoamyl acetate, then mixing until dissolved;
   vi) if needed, adjusting pH to 5.4-5.6 with a 50% w/w NaOH solution or acetic acid; and
   vii) if needed, adding sufficient water to provide a total weight consistent with the total batch size.

30. A method of treating Charcot-Marie-Tooth disease of type 1A (CMT1A), comprising administering the composition of claim 1 to a human subject in need thereof.

31. A container comprising the composition of claim 1.

32. A container comprising the composition of claim 1 in a volume of 100 mL.

33. A patient pack comprising a set of single-dose sachets or ampoules containing the composition of claim 1 in a suitable amount for treating CMT1A in a human subject in need thereof.

34. A pharmaceutical kit of parts comprising a bottle comprising the composition of claim 1; a cap or a pipette or a pipette-cap system; and optionally instructions for administration of the composition.

35. A pharmaceutical kit of parts that allows preparation of the composition of claim 1, and optionally instructions for preparing the composition.

* * * * *